United States Patent
Klein (10) Patent No.: US 9,744,231 B2
(45) Date of Patent: *Aug. 29, 2017

(54) QUALITY CONTROL METHODS FOR OIL-IN-WATER EMULSIONS CONTAINING SQUALENE

(71) Applicant: Novartis AG, Basel (CH)

(72) Inventor: Norbert Klein, Cambridge, MA (US)

(73) Assignee: NOVARTIS AG, Basel (CH)

( * ) Notice: Subject to any disclaimer, the term of this patent is extended or adjusted under 35 U.S.C. 154(b) by 431 days.

This patent is subject to a terminal disclaimer.

(21) Appl. No.: 14/011,258

(22) Filed: Aug. 27, 2013

(65) Prior Publication Data

US 2014/0178428 A1   Jun. 26, 2014

Related U.S. Application Data

(63) Continuation of application No. 12/312,629, filed as application No. PCT/IB2007/004229 on Nov. 6, 2007, now Pat. No. 8,562,943.

(30) Foreign Application Priority Data

Nov. 8, 2006   (GB) .................................. 06222822

(51) Int. Cl.
| | |
|---|---|
| A61K 39/39 | (2006.01) |
| A61K 39/145 | (2006.01) |
| A61K 9/10 | (2006.01) |
| A61K 47/26 | (2006.01) |
| A61K 39/00 | (2006.01) |

(52) U.S. Cl.
CPC ............... *A61K 39/39* (2013.01); *A61K 9/10* (2013.01); *A61K 39/145* (2013.01); *A61K 47/26* (2013.01); *A61K 2039/55566* (2013.01); *Y10T 436/216* (2015.01)

(58) Field of Classification Search
None
See application file for complete search history.

(56) References Cited

U.S. PATENT DOCUMENTS

| | | | |
|---|---|---|---|
| 6,861,410 B1 | 3/2005 | Ott et al. | |
| 8,562,943 B2 * | 10/2013 | Klein ....................... | A61K 9/10 424/1.11 |
| 2007/0141078 A1 | 6/2007 | D'Hondt et al. | |

FOREIGN PATENT DOCUMENTS

| | | |
|---|---|---|
| CN | 1399539 | 2/2003 |
| EP | 0399843 | 11/1990 |
| EP | 0745387 | 12/1996 |
| EP | 0868918 | 4/2004 |
| WO | WO 90/14837 | 12/1990 |
| WO | WO 99/02132 | 1/1999 |
| WO | WO 01/21152 A1 | 3/2001 |
| WO | WO 2006/100110 | 9/2006 |
| WO | WO 2007/006939 | 1/2007 |

OTHER PUBLICATIONS

Allison, "Squalene and Squalane Emulsions as Adjuvants", Methods, 19:87-93 (1999).
Bauer, Pharmaceutical Packaging Handbook, Informa Healthcare, p. 196 (2009).
Derek T. O'Hagan, "MF59 is a Safe and Potent Vaccine Adjuvant That Enhances Protection Against Influenza Virus Infection," Expert Rev. Vaccines, 6(5):699-711 (2007).
Lidgate et al., "Sterile Filtration of a Parenteral Emulsion", Pharmaceutical Research, vol. 9, No. 7, (1992).
Miles et al., "Montanider ISA 720 Vaccines: Quality Control of Emulsions, Stability of Formulated Antigens, and Comparative Immunogenicity of Vaccine Formulations," Vaccine, Butterworth Scientific, Guildfor, GB, 23(19):2530-2539 (2005).
Ott et al., "The Adjuvant MF:59: A 10-Year Perspective," Methods in Molecular Medicine, 42:211-228 (2000).
Ott et al., "The Adjuvant MF59: A 10-Year Perspective", Vaccine Adjuvants: Preparation Methods and Research Protocols, Methods in Molecular Medicine, vol. 42, (2000).
Ott et al., "MF59—Design and Evaluation of a Safe NAD Potent Adjuvant for Human Vaccines", Vaccine Design, the Subunit and Adjuvant Approach, Pharmaceutical Biotechnology, 6:277-296 (1995).
Sorgi et al., "Large Scale Production of DC-CHOL Cationic Liposomes by Microfluidization", International Journal of Pharmaceuticals, 144:131-139 (1996).
Spanggord et al., "Enhancement of an Analytical Method for the Determination of Squalene in Anthrax Vaccine Absorbed Formulations," Journal of Pharmaceutical and Biomedical Analysis, New York, 42(4):494-499 (2006).
Suli et al., "Experimental Squalene Adjuvant I. Preparation and Testing of Its Effectiveness," Vaccine, 22:3464-3469 (2004).
Wack et al., "Combination Adjuvants for the Induction of Potent, Long-Lasting Antibody and T-Cell Responses to Influenza Vaccine in Mice," Vaccine, Butterworth Scientific, Guildford, GB, 26(4):552-561 (2007).
European Commission, "EC Guide to Good Manufacturing Practice Revision to ANNEX1", May 30, 2003.
Patentee's Response to Opposition, European Patent No. 2029170B1, Novartis Ag, 07859275.5/O007255EP, 20 pages, Mar. 11, 2011.

(Continued)

*Primary Examiner* — Benjamin P Blumel
(74) *Attorney, Agent, or Firm* — Vedder Price P.C.; Thomas J. Kowalski; Mark W. Russell (57) ABSTRACT

Measurements of the squalene content in oil-in-water emulsions can be used as a way of checking for problems during production. In particular, it has been found that a drop in squalene content can indicate that filtration problems occurred. Testing the squalene content in the final lots is easier than investigating the characteristics of the filter, and so a squalene assay simplifies the quality control of oil-in-water emulsions.

11 Claims, 1 Drawing Sheet

(56) References Cited

OTHER PUBLICATIONS

Notice of Opposition to a European Patent, Opposition against the grant of European Patent EP2029170B1, Patent Application No. 07859275, 27 pages, Jul. 27, 2010.
Notice of Opposition to a European Patent, Opposition against the grant of European Patent EP2029170B1, Patent Application No. 07859275, 17 pages, Jul. 28, 2010.
Notice of Opposition to a European Patent, Opposition against the grant of European Patent EP2029170B1, Patent Application No. 07859275, 15 pages, Jul. 27, 2010.
Decision revoking the European Patent No. EP2029170B1, Patent Application No. 07859275, 13 pages, dated Jul. 18, 2012.
The Rules Governing Medicinal Products in the EU, vol. 4, "Good Manufacturing Practices", 1997 Edition of European Commission, Dir. III, pp. III-X, 3-9, 22-25, 43-52.
Notice of Appeal in the European Patent No. EP2029170B1, Patent Application No. 07859275, 1 page, dated Sep. 27, 2012.
Statement of Grounds of Appeal in the European Patent No. EP2029170B1, Patent Application No. 07859275, 18 pages, dated Nov. 28, 2012.

* cited by examiner

QUALITY CONTROL METHODS FOR OIL-IN-WATER EMULSIONS CONTAINING SQUALENE

CROSS-REFERENCE TO RELATED APPLICATIONS

This application is a continuation application of U.S. patent application Ser. No. 12/312,629, filed May 18, 2009, which is a §371 filing of International Application No. PCT/IB2007/004229, filed Nov. 6, 2007, which claims priority to G.B. Application No. 0622282.2, filed Nov. 8, 2006, from which applications priority is claimed pursuant to 35 U.S.C. §§119/120, which applications are hereby incorporated by reference in their entireties.

TECHNICAL FIELD

This invention is in the field of vaccine adjuvant manufacture and, in particular, quality control assays for oil-in-water emulsion adjuvants that contain squalene.

BACKGROUND ART

The vaccine adjuvant known as 'MF59' [1-3] is a submicron oil-in-water emulsion of squalene, Tween 80, and Span 85. It may also includes citrate ions e.g. 10 mM sodium citrate buffer. The composition of the emulsion by volume can be about 5% squalene, about 0.5% polysorbate 80 and about 0.5% Span 85. The adjuvant is described in more detail in Chapter 10 of ref. 4 and chapter 12 of ref. 5. The oil droplets in MF59 are small enough to be sterile-filtered through a 0.2 μm filter.

Because it is an adjuvant for administration to humans (e.g. it is included in the FLUAD™ vaccine) then quality control of the vaccine is particularly important, and lot-to-lot variation has to be controlled within narrow limits. Parameters that are important for MF59 include the mean droplet size in the emulsion, the bioburden, the pH, the visual appearance, and the presence of breakdown products or of common contaminants of its ingredients.

It is an object of the invention to provide further and improved assays for quality control of oil-in-water emulsion adjuvants such as MF59.

DISCLOSURE OF THE INVENTION

It has now been found that measurements of the squalene content in lots of the MF59 adjuvant can be used as a way of checking for problems during production. In particular, it has been found that a drop in squalene content can indicate that filtration problems occurred. Testing the squalene content in the final lots is easier than investigating the characteristics of the filter, particularly if the filter is part of an apparatus that is being maintained in GMP conditions, and so a squalene assay simplifies the quality control of oil-in-water emulsions.

Thus the invention provides a quality control test method for an oil-in-water emulsion adjuvant, wherein the adjuvant comprises squalene, and wherein the method comprises a step of comparing the actual squalene content of the adjuvant to a standard squalene content. If the actual squalene content differs from the standard content then there has been a production failure and so the adjuvant fails the quality control test; if the actual content is acceptable, however, the adjuvant passes the quality control test and can be used for vaccine manufacture.

The invention also provides a process for manufacturing an oil-in-water emulsion adjuvant, comprising the steps of: (i) preparing a submicron oil-in-water emulsion using known amounts of an aqueous carrier, a surfactant and squalene; (ii) subjecting the emulsion to filter sterilization, to provide a sterilized emulsion; and (iii) measuring the squalene content of the sterilized emulsion. The squalene content measured in step (iii) can be compared to the squalene content known from step (i). If this comparison reveals that the squalene content has significantly changed then there has been a production failure and so the adjuvant fails the quality control test.

Before being administered to a patient, an emulsion adjuvant is usually admixed with an antigen. The mixing may take place extemporaneously, at the time of use (in which case the antigen and adjuvant are packaged separately), or can take place during vaccine manufacture, before filling. In the former situation, the quality control test will be performed on the adjuvant itself. In the latter situation, the quality control test may take place on the adjuvant before being mixed with the antigen and/or on the adjuvant-antigen admixture.

Thus the invention also provides a quality control test method for a vaccine that includes an oil-in-water emulsion adjuvant including squalene, wherein the method comprises the steps of: (i) comparing the actual squalene content of the adjuvant to a standard squalene content; and, if the actual squalene content is acceptable, (ii) preparing the vaccine by combining the adjuvant with an antigen. Step (ii) may involve packaging the adjuvant and antigen separately, such that they can be admixed at the time of use, or it may involve admixing them before or during filling.

Similarly, the invention provides a quality control test method for a vaccine that includes an antigen and an oil-in-water emulsion adjuvant including squalene, wherein the method comprises a step of comparing the actual squalene content of the vaccine to a standard squalene content. If the actual squalene content differs from the standard content then there has been a production failure and so the vaccine fails the quality control test; if the actual content is acceptable, however, the vaccine passes the quality control test and can be released for sale and/or distribution.

The invention is particularly useful during the manufacture of influenza virus vaccines, and so the invention provides a method comprising a step of mixing (i) an influenza virus antigen and (ii) an oil-in-water emulsion adjuvant that includes squalene, and wherein the method also includes a step in which squalene content is measured (a) in the adjuvant before the mixing step and/or (b) in the antigen-adjuvant mixture after the mixing step. As mentioned above, the measured squalene content(s) can be compared to standard squalene content(s) in order to check for production failure.

The Testing Method

The methods of the invention are used with oil-in-water emulsion adjuvants that include squalene, and involve measuring the squalene content of either (i) the adjuvant itself, and/or (ii) a vaccine composition that includes the adjuvant in admixture with an antigen.

Various squalene assays are known in the art. For example, reference 6 discloses a quantitative colorimetric assay for squalene. Reference 7 discloses a high-temperature gas chromatography flame ionization detection method for quantification of squalene in the presence of free fatty acids, free sterols and acylglycerol molecular species. Reference 8 discloses a validated assay using high performance liquid chromatography with ultraviolet detection, with a limit of detection of 140 parts per billion. Reference 9 discloses the use of supercritical fluid chromatography in the quantitative analysis of squalene. Reference 10 discloses laser desorption/ionization time-of-flight mass spectrometry methods for assaying squalene. Reference 11 discloses the use of gas chromatography-mass spectrometry and high-performance liquid chromatography with supercritical $CO_2$ extraction for assaying squalene content. Reference 12 discloses a simple and reliable procedure for the quantification of squalene, α-tocopherol and sterols by a direct method involving gas chromatographic analysis of unsaponifiable material after silylation. Reference 13 discloses a procedure where unsaponifiable material is fractionated by normal phase HPLC on a silica gel column using a mobile phase consisting of hexane/propanol-2/water, the eluate is monitored at 215 nm, and squalene in the hydrocarbon fraction thus collected is quantified on an analytical column eluted with hexane. Direct and indirect assays can be used e.g. squalene may first be subjected to cold saponification, followed by gas chromatography-mass spectrometry of the hexane extract.

When the squalene content of an adjuvant or an antigen has been measured, it is compared to a standard squalene content. A standard squalene content can be an amount which is known to be acceptable for administration to patients for the adjuvant in question. It can be the amount of squalene that was used to prepare the adjuvant, thereby allowing the final amount of squalene to be compared to the starting amount.

The standard content may be provided in various forms. For instance, a positive control sample of adjuvant can be assayed in parallel to the test adjuvant, such that their squalene contents can be compared. As an alternative, the positive control could be analysed before or after the test adjuvant to provide a figure for comparison. As a further alternative, the standard content may be an absolute figure based on previous analyses. In all cases, however, the method will reveal if the squalene content in the adjuvant being tested is acceptable for quality control purposes. If the measured squalene content differs from the standard content then this difference indicates a production failure.

The standard content may be an absolute amount or concentration, or it may be a relative amount e.g. measured relative to surfactant content or to antigen content. An absolute amount or concentration is more usual.

The standard content may be a precise figure or may be a range. For instance, it may be an absolute amount with an acceptable percentage deviation e.g. ±10%, ±5%, etc. A measured content can then be compared to a standard content range and, if it falls outside the range, the assay is failed. Typical absolute standard squalene contents for oil-in-water emulsion adjuvants may be, for instance, between 40-45 mg/ml (e.g. 43 mg/ml), between 36-42 mg/ml (e.g. 39 mg/ml), between 20-25 mg/ml (e.g. 21.5 mg/ml), between 18-21 mg/ml (e.g. 19.5 mg/ml), etc.

In accordance with normal statistical standards, squalene content will typically be measured for several samples in order to minimise the effects of experimental deviation. Thus the invention may involve a comparison of an average value against the standard content.

As explained in more detail below, the squalene assay can be performed on an adjuvant before being mixed with antigen, on antigen/adjuvant mixtures, on bulk material prior to filling, on filled material that has been extracted from bulks, etc.

The Adjuvant

The methods of the invention are used with oil-in-water emulsion adjuvants. The adjuvants include squalene, which is an unsaturated terpenoid oil ($C_{30}H_{50}$; [$(CH_3)_2C$[=$CHCH_2CH_2C(CH_3)$]$_2$=$CHCH_2$—]$_2$; 2,6,10,15,19,23-hexamethyl-2,6,10,14,18,22-tetracosahexaene; CAS RN 7683-64-9).

The adjuvants may also include other oils in addition to squalene. Preferably, any further oils are biodegradable (metabolisable) and biocompatible. The adjuvants may also include oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids, which include squalene. Squalane, the saturated analog to squalene, can also be used. Fish oils, including squalene and squalane, are readily available from commercial sources or may be obtained by methods known in the art. Other preferred oils are the tocopherols. Where a composition includes a tocopherol, any of the α, β, γ, δ, ε or ξ tocopherols can be used, but α-tocopherols are preferred. The tocopherol can take several forms e.g. different salts and/or isomers. Salts include organic salts, such as succinate, acetate, nicotinate, etc. D-α-tocopherol and DL-α-tocopherol can both be used. A preferred α-tocopherol is DL-α-tocopherol. If a salt of this tocopherol is to be used, the preferred salt is the succinate.

In addition to the presence of squalene (and, optionally, one or more further other oils), the emulsion includes an aqueous phase and a surfactant. The surfactant is preferably biodegradable (metabolisable) and biocompatible. Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy) polyethoxyethanol (IGEPAL CA-630/NP-40); phospholipids such as phosphatidylcholine(lecithin); polyoxyethylene fatty ethers derived from lauryl, cetyl, stearyl and oleyl alcohols (known as Brij surfactants), such as triethyleneglycol monolauryl ether (Brij 30); polyoxyethylene-9-lauryl ether; and sorbitan esters (commonly known as the SPANs), such as sorbitan trioleate (Span 85) and sorbitan monolaurate. Preferred surfactants for including in the emulsion are Tween 80 (polyoxyethylene sorbitan monooleate), Span 85 (sorbitan trioleate), lecithin and Triton X-100.

Mixtures of surfactants can be used e.g. Tween 80/Span 85 mixtures, or Tween 80/Triton-X100 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

The aqueous phase of the emulsion is preferably buffered e.g. phosphate buffered saline.

The oil droplets in the emulsion are typically less than 1 μm in diameter (on average). Sub-micron diameters can easily be achieved with a microfluidiser to provide stable emulsions. Droplets with a size less than 220 nm are particularly preferred, as they can be subjected to filter sterilization. Emulsions in which at least 80% by number of the droplets have a diameter in the range of 50-200 nm are particularly useful.

Specific oil-in-water emulsion adjuvants that contain squalene and can be tested by the methods of the invention include, but are not limited to:

A submicron emulsion of squalene, Tween 80, and Span 85. The composition of the emulsion by volume can be about 5% squalene, about 0.5% polysorbate 80 and about 0.5% Span 85. In weight terms, these amounts become 4.3% squalene, 0.5% polysorbate 80 and 0.48% Span 85. This adjuvant is known as 'MF59'. The MF59 emulsion advantageously includes citrate ions e.g. 10 mM sodium citrate buffer.

An emulsion of squalene, a tocopherol, and Tween 80. The emulsion may include phosphate buffered saline. It may also include Span 85 (e.g. at 1%) and/or lecithin. These emulsions may have from 2 to 10% squalene, from 2 to 10% tocopherol and from 0.3 to 3% Tween 80, and the weight ratio of squalene:tocopherol is preferably ≤1 as this provides a more stable emulsion. Squalene and Tween 80 may be present volume ratio of about 5:2. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm. The emulsion may also include a 3d-MPL and/or a saponin (e.g. QS21).

An emulsion of squalene, a tocopherol, and a Triton detergent (e.g. Triton X-100). The emulsion may also include a 3-O-deacylated monophosphoryl lipid A ('3d-MPL'). The emulsion may contain a phosphate buffer.

An emulsion comprising squalene, Pluronic F-68 block co-polymer, egg phosphatidyl choline, glycerol and a tocopherol [14].

An emulsion comprising squalene, a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 μg/ml polysorbate 80, 110 μg/ml Triton X-100 and 100 μg/ml α-tocopherol succinate), and these concentrations should include any contribution of these components from antigens. The emulsion may also include a 3d-MPL. The emulsion may also include a saponin, such as QS21. The aqueous phase may contain a phosphate buffer.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [15]. The emulsion may also include one or more of: alditol; a cryoprotective agent (e.g. a sugar, such as dodecylmaltoside and/or sucrose); and/or an alkylpolyglycoside. It may also include a TLR4 agonist, such as one whose chemical structure does not include a sugar ring [16]. Such emulsions may be lyophilized.

An emulsion of squalene, poloxamer 105 and Abil-Care [17]. The final concentration (weight) of these components in adjuvanted vaccines are 5% squalene, 4% poloxamer 105 (pluronic polyol) and 2% Abil-Care 85 (Bis-PEG/PPG-16/16 PEG/PPG-16/16 dimethicone; caprylic/capric triglyceride).

The Antigen

Although it is possible to administer oil-in-water emulsion adjuvants on their own to patients (e.g. to provide an adjuvant effect for an antigen that has been separately administered to the patient), it is more usual to admix the adjuvant with an antigen prior to administration. This admixing may take place during manufacture, such that the distributed vaccine product is ready for administration, or can take place at the time of use.

Various antigens can be used with oil-in-water emulsions, including but not limited to: viral antigens, such as viral surface proteins; bacterial antigens, such as protein and/or saccharide antigens; fungal antigens; parasite antigens; and tumor antigens.

The invention is particularly useful for vaccines against influenza virus, HIV, hookworm, hepatitis B virus, herpes simplex virus, rabies, respiratory syncytial virus, cytomegalovirus, *Staphylococcus aureus*, chlamydia, SARS coronavirus, varicella zoster virus, *Streptococcus pneumoniae, Mycobacterium tuberculosis, Bacillus anthracis*, Epstein Barr virus, human papillomavirus, etc.

Influenza virus antigens. These may take the form of a live virus or an inactivated virus. Where an inactivated virus is used, the vaccine may comprise whole virion, split virion, or purified surface antigens (including hemagglutinin and, usually, also including neuraminidase). Influenza antigens can also be presented in the form of virosomes [18]. The antigens may have any hemagglutinin subtype, selected from H1, H2, H3, H4, H5, H6, H7, H8, H9, H10, H11, H12, H13, H14, H15 and/or H16. Vaccine may include antigen(s) from one or more (e.g. 1, 2, 3, 4 or more) influenza virus strains, including influenza A virus and/or influenza B virus. The influenza virus may be a reassortant strain, and may have been obtained by reverse genetics techniques [e.g. 19-23]. Thus the virus may include one or more RNA segments from a A/PR/8/34 virus (typically 6 segments from A/PR/8/34, with the HA and N segments being from a vaccine strain, i.e. a 6:2 reassortant). The viruses used as the source of the antigens can be grown either on eggs (e.g. embryonated hen eggs) or on cell culture. Where cell culture is used, the cell substrate will typically be a mammalian cell line, such as MDCK; CHO; 293T; BHK; Vero; MRC-5; PER.C6; WI-38; etc. Preferred mammalian cell lines for growing influenza viruses include: MDCK cells [24-27], derived from Madin Darby canine kidney; Vero cells [28-30], derived from African green monkey (*Cercopithecus aethiops*) kidney; or PER.C6 cells [31], derived from human embryonic retinoblasts. These cell lines are widely available e.g. from the American Type Cell Culture (ATCC) collection [32], from the Coriell Cell Repositories [33], or from the European Collection of Cell Cultures (ECACC). For example, the ATCC supplies various different Vero cells under catalog numbers CCL-81, CCL-81.2, CRL-1586 and CRL-1587, and it supplies MDCK cells under catalog number CCL-34. PER.C6 is available from the ECACC under deposit number 96022940. As a less-preferred alternative to mammalian cell lines, virus can be grown on avian cell lines [e.g. refs. 34-36], including cell lines derived from ducks (e.g. duck retina) or hens e.g. chicken embryo fibroblasts (CEF), etc. Where virus has been grown on a mammalian cell line then the composition will advantageously be free from egg proteins (e.g. ovalbumin and ovomucoid) and from chicken DNA, thereby reducing allergenicity.

Human immunodeficiency virus, including HIV-1 and HIV-2. The antigen will typically be an envelope antigen.

Hepatitis B virus surface antigens. This antigen is preferably obtained by recombinant DNA methods e.g. after expression in a *Saccharomyces cerevisiae* yeast. Unlike native viral HBsAg, the recombinant yeast-expressed antigen is non-glycosylated. It can be in the form of substantially-spherical particles (average diameter of about 20 nm), including a lipid matrix comprising phospholipids. Unlike native HBsAg particles, the yeast-expressed particles may include phosphatidylinositol. The HBsAg may be from any of subtypes ayw1, ayw2, ayw3, ayw4, ayr, adw2, adw4, adrq− and adrq+.

Hookworm, particularly as seen in canines (*Ancylostoma caninum*). This antigen may be recombinant Ac-MTP-1 (astacin-like metalloprotease) and/or an aspartic hemoglobinase (Ac-APR-1), which may be expressed in a baculovirus/insect cell system as a secreted protein [37,38].

Herpes simplex virus antigens (HSV). A preferred HSV antigen for use with the invention is membrane glycoprotein gD. It is preferred to use gD from a HSV-2 strain ('gD2' antigen). The composition can use a form of gD in which the C-terminal membrane anchor region has been deleted [39] e.g. a truncated gD comprising amino acids 1-306 of the natural protein with the addition of aparagine and glutamine at the C-terminus. This form of the protein includes the signal peptide which is cleaved to yield a mature 283 amino acid protein. Deletion of the anchor allows the protein to be prepared in soluble form.

Human papillomavirus antigens (HPV). Preferred HPV antigens for use with the invention are L1 capsid proteins, which can assemble to form structures known as virus-like particles (VLPs). The VLPs can be produced by recombinant expression of L1 in yeast cells (e.g. in *S. cerevisiae*) or in insect cells (e.g. in *Spodoptera* cells, such as *S. frugiperda*, or in *Drosophila* cells). For yeast cells, plasmid vectors can carry the L1 gene(s); for insect cells, baculovirus vectors can carry the L1 gene(s). More preferably, the composition includes L1 VLPs from both HPV-16 and HPV-18 strains. This bivalent combination has been shown to be highly effective [40]. In addition to HPV-16 and HPV-18 strains, it is also possible to include L1 VLPs from HPV-6 and HPV-11 strains. The use of oncogenic HPV strains is also possible. A vaccine may include between 20-60 μg/ml (e.g. about 40 μg/ml) of L1 per HPV strain.

Anthrax antigens. Anthrax is caused by *Bacillus anthracis*. Suitable *B. anthracis* antigens include A-components (lethal factor (LF) and edema factor (EF)), both of which can share a common B-component known as protective antigen (PA). The antigens may optionally be detoxified. Further details can be found in references 41 to 43].

Cancer antigens. A variety of tumour-specific antigens are known. The invention may be used with antigens that elicit an immunotherapeutic response against lung cancer, melanoma, breast cancer, prostate cancer, etc.

The invention is also useful with antigens based on hybrid or fusion proteins that comprise a viral surface antigen and a heterologous antigen. For instance, it is known to fuse the HBsAg sequence to heterologous antigens to exploit HBsAg's ability to assemble into particles. For example, reference 44 reports fusions of HIV-1 gp120 to HBsAg to give a protein that spontaneously assembled into particles that resemble native HBsAg particles. This approach has also been used for malaria vaccines. Reference 45 reports that epitopes of up to 61aa from the malaria gp190 antigen were inserted into the HBsAg sequence, and that the expressed hybrid particles could elicit an anti-gp190 immune response in animals. Reference 46 report an protein having 16 repeats of a 4-mer sequence of the circumsporozoite protein expressed as a fusion protein with HBsAg. Reference 47 reports the production in yeast of virus-like particles composed of Pfs16 fused to HBsAg. Reference 48 discloses a hybrid antigen in which the circumsporozoite protein is fused to HBsAg. Reference 49 discloses a fusion of the C-terminal region of the merozoite surface 1 protein of *P. vivax*, which formed immunogenic particles of 20-45 nm size. The use of HBsAg for presenting malarial antigens in self-assembling particulate form is therefore well known in the art. Thus the invention can be used with hybrid antigens that comprise a viral surface antigen and a heterologous antigen. Particularly where the viral surface antigen is HBsAg, the heterologous antigen may be from HIV, *Plasmodium falciparum, Plasmodium vivax, Plasmodium malariae* or *Plasmodium ovale*. Suitable HIV antigens for making HBsAg hybrids include envelope glycoprotein gp120 or antigenic fragments thereof [44]. Suitable *P. falciparum* antigens for making HBsAg hybrids may be based on a subunit of the circumsporozoite surface antigen ("CSP") e.g. they may include between 3 and 20 repeats of its NANP motif, and/or they may include the C-terminal region of CSP (but typically not including the final 12 amino acids from the C-terminal). For example, the invention may use the antigen known as "RTS", which contains a large portion of the C-terminal of CSP from the NF54 or 7G8 isolate of *P. falciparum* (amino acids 210 to 398, which includes 19 NANP repeats and the T cell epitope region at amino acids 367 to 390), fused to the N-terminus of HBsAg by four amino acids of the preS2 portion of HBsAg. The sequence of RTS can thus contain: (i) a N-terminus methionine residue; (ii) Met-Ala-Pro; (iii) 189 amino acids corresponding either to amino acids 210-398 of CS protein from *P. falciparum* 7G8 or to amino acids 207-395 of CS protein from *P. falciparum* NF54; (iv) Arg or Gly; (v) Pro-Val-Thr-Asn from hepatitis B Pre-S2 protein; and (vi) HBsAg.

The Vaccine

Emulsion adjuvants that have been tested by the methods of the invention can be used to manufacture vaccines. As mentioned above, mixing and emulsion and antigen may take place extemporaneously, at the time of use, or can take place during vaccine manufacture. The methods of the invention can be applied when making both types of vaccine. For a pre-mixed vaccine, the method can be performed on the adjuvant before it is mixed with antigen, and/or it can be performed after mixing, and vaccine that passes quality control testing can then be released for sale and/or distribution. For a vaccine supplied in a form for extemporaneous mixing, the method will be performed on the adjuvant prior to packaging it in a kit together with antigen.

Thus a method of the invention which tests an adjuvant may include a further process step of admixing the adjuvant with an antigen. As an alternative, it may include a further step of packaging the adjuvant into a kit as a kit component together with an antigen component. These further steps will usually take place only if the adjuvant has passed the quality control test.

Methods of the invention will usually be performed on a small sample of a bulk adjuvant or admixed vaccine. Quality control will be performed on this sample, and the bulk will be packaged into doses only if the sample passes the quality control test. Thus a method of the invention may involve: extracting a sample from a bulk adjuvant; testing that sample as described above; and then, if the sample passes the test, combining that bulk with a bulk mixture of antigen. Unit doses of the mixed bulks can then be extracted and packaged for sale and/or distribution.

In an alternative embodiment, a method of the invention may involve: extracting a sample from a bulk adjuvant; testing that sample, as described above; and then, if the sample passes the test, extracting unit doses from the bulk adjuvant for mixing with unit doses of antigen.

In a further alternative embodiment, a method of the invention may involve: extracting a sample from a bulk adjuvant; testing that sample as described above; and then, if the sample passes the test, extracting unit doses from the bulk adjuvant for packaging as kit components, as described above, for extemporaneous use.

In a further alternative embodiment, a method of the invention may involve: extracting a sample from a bulk mixture of antigen and adjuvant; testing that sample, as described above; and then, if the sample passes the test, extracting unit doses from the bulk mixture for packaging.

For influenza vaccines, unit doses of vaccine are typically standardized by reference to hemagglutinin (HA) content, typically measured by SRID. Existing vaccines typically contain about 15 µg of HA per strain, although lower doses can be used, particularly when using an adjuvant. Fractional doses such as ½ (i.e. 7.5 µg HA per strain), ¼ and ⅛ have been used [50,51], as have higher doses (e.g. 3× or 9× doses [52,53]). Thus vaccines may include between 0.1 and 150 µg of HA per influenza strain, preferably between 0.1 and 50 µg e.g. 0.1-20 µg, 0.1-15 µg, 0.1-10 µg, 0.1-7.5 µg, 0.5-5 µg, etc. Particular doses include e.g. about 15, about 10, about 7.5, about 5, about 3.8, about 1.9, about 1.5, etc. per strain.

Overall, therefore, the invention can be used when preparing mixed vaccines or when preparing kits including antigen and adjuvant ready for mixing. Where mixing takes place during manufacture then the volumes of bulk antigen and adjuvant that are mixed will typically be greater than 1 liter e.g. ≥5 liters, ≥10 liters, ≥20 liters, ≥50 liters, etc. Where mixing takes place at the point of use then the volumes that are mixed will typically be smaller than 1 milliliter e.g. ≤0.6 ml, ≤0.5 ml, ≤0.4 ml, ≤0.3 ml, ≤0.2 ml, etc. In both cases it is usual for substantially equal volumes of emulsion and antigen solution to be mixed i.e. substantially 1:1 (e.g. between 1.1:1 and 1:1.1, preferably between 1.05:1 and 1:1.05, and more preferably between 1.025:1 and 1:1.025). In some embodiments, however, an excess of adjuvant or an excess of antigen may be used. Where an excess volume of one component is used, the excess will generally be at least 1.5:1 e.g. ≥2:1, ≥2.5:1, ≥3:1, ≥4:1, ≥5:1, etc.

Where antigen and adjuvant are presented as separate components within a kit, they are physically separate from each other within the kit, and this separation can be achieved in various ways. For instance, the components may be in separate containers, such as vials. The contents of two vials can then be mixed when needed e.g. by removing the contents of one vial and adding them to the other vial, or by separately removing the contents of both vials and mixing them in a third container.

In a preferred arrangement, one of the kit components is in a syringe and the other is in a container such as a vial. The syringe can be used (e.g. with a needle) to insert its contents into the second container for mixing, and the mixture can then be withdrawn into the syringe. The mixed contents of the syringe can then be administered to a patient, typically through a new sterile needle. Packing one component in a syringe eliminates the need for using a separate syringe for patient administration.

In another preferred arrangement, the two kit components are held together but separately in the same syringe e.g. a dual-chamber syringe, such as those disclosed in references 54-61 etc. When the syringe is actuated (e.g. during administration to a patient) then the contents of the two chambers are mixed. This arrangement avoids the need for a separate mixing step at the time of use.

The contents of the various kit components will generally all be in aqueous form. In some arrangements, a component (typically the antigen component rather than the emulsion component) is in dry form (e.g. in a lyophilised form), with the other component being in aqueous form. The two components can be mixed in order to reactivate the dry component and give an aqueous composition for administration to a patient. A lyophilised component will typically be located within a vial rather than a syringe. Dried components may include stabilizers such as lactose, sucrose or mannitol, as well as mixtures thereof e.g. lactose/sucrose mixtures, sucrose/mannitol mixtures, etc. One possible arrangement uses an aqueous emulsion component in a pre-filled syringe and a lyophilised antigen component in a vial.

If vaccines contain components in addition to the adjuvant and the antigen then these further components may be included in one these two kit components, or may be part of a third kit component.

Suitable containers for mixed vaccines of the invention, or for individual kit components, include vials and disposable syringes. These containers should be sterile.

Where a composition/component is located in a vial, the vial is preferably made of a glass or plastic material. The vial is preferably sterilized before the composition is added to it. To avoid problems with latex-sensitive patients, vials are preferably sealed with a latex-free stopper, and the absence of latex in all packaging material is preferred. The vial may include a single dose of vaccine, or it may include more than one dose (a 'multidose' vial) e.g. 10 doses. Preferred vials are made of colorless glass.

A vial can have a cap (e.g. a Luer lock) adapted such that a pre-filled syringe can be inserted into the cap, the contents of the syringe can be expelled into the vial (e.g. to reconstitute lyophilised material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed.

Where a composition/component is packaged into a syringe, the syringe will not normally have a needle attached to it, although a separate needle may be supplied with the syringe for assembly and use. Safety needles are preferred. 1-inch 23-gauge, 1-inch 25-gauge and ⅝-inch 25-gauge needles are typical. Syringes may be provided with peel-off labels on which the lot number, influenza season and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of a butyl rubber. If the syringe and needle are packaged separately then the needle is preferably fitted with a butyl rubber shield. Preferred syringes are those marketed under the trade name "Tip-Lok"™.

Containers may be marked to show a half-dose volume e.g. to facilitate delivery to children. For instance, a syringe containing a 0.5 ml dose may have a mark showing a 0.25 ml volume.

Where a glass container (e.g. a syringe or a vial) is used, then it is preferred to use a container made from a borosilicate glass rather than from a soda lime glass.

A kit or composition may be packaged (e.g. in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

Pharmaceutical Compositions

Compositions made using the methods of the invention are pharmaceutically acceptable. They may include components in addition to the antigen and adjuvant e.g. they will typically include one or more pharmaceutical carrier(s) and/or excipient(s). A thorough discussion of such components is available in reference 62.

The composition may include preservatives such as thiomersal or 2-phenoxyethanol. It is preferred, however, that the vaccine should be substantially free from (i.e. less than 5 µg/ml) mercurial material e.g. thiomersal-free [63,64]. Vaccines containing no mercury are more preferred.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg. Osmolality has previously been reported not to have an impact on pain caused by vaccination [65], but keeping osmolality in this range is nevertheless preferred.

Compositions may include one or more buffers. Typical buffers include: a phosphate buffer; a Tris buffer; a borate buffer; a succinate buffer; a histidine buffer; or a citrate buffer. Buffers will typically be included in the 5-20 mM range.

The pH of a composition will generally be between 5.0 and 8.1, and more typically between 6.0 and 8.0 e.g. between 6.5 and 7.5. A process of the invention may therefore include a step of adjusting the pH of the bulk vaccine prior to packaging.

The composition is preferably sterile. The composition is preferably non-pyrogenic e.g. containing <1 EU (endotoxin unit, a standard measure) per dose, and preferably <0.1 EU per dose. The composition is preferably gluten free.

The composition may include material for a single immunisation, or may include material for multiple immunisations (i.e. a 'multidose' kit). The inclusion of a preservative is preferred in multidose arrangements.

Vaccines are typically administered in a dosage volume of about 0.5 ml, although a half dose (i.e. about 0.25 ml) may be administered to children.

Compositions and kits are preferably stored at between 2° C. and 8° C. They should not be frozen. They should ideally be kept out of direct light.

Methods of Treatment, and Administration of the Vaccine

The invention provides kits and compositions prepared using the methods of the invention. These are suitable for administration to human patients, and the invention provides a method of raising an immune response in a patient, comprising the step of administering such a composition to the patient.

The invention also provides these kits and compositions for use as medicaments.

The invention also provides the use of: (i) an aqueous preparation of an antigen; and (ii) an oil-in-water emulsion adjuvant tested according to the invention, in the manufacture of a medicament for raising an immune response in a patient.

The immune response raised by these methods and uses will generally include an antibody response, preferably a protective antibody response.

The compositions can be administered in various ways. The most preferred immunisation route is by intramuscular injection (e.g. into the arm or leg), but other available routes include subcutaneous injection, intranasal [66-68], oral [69], intradermal [70,71], transcutaneous, transdermal [72], etc.

Vaccines prepared according to the invention may be used to treat both children and adults. The patient may be less than 1 year old, 1-5 years old, 5-15 years old, 15-55 years old, or at least 55 years old. The patient may be elderly (e.g. ≥50 years old, preferably ≥65 years), the young (e.g. ≤5 years old), hospitalised patients, healthcare workers, armed service and military personnel, pregnant women, the chronically ill, immunodeficient patients, and people travelling abroad. The vaccines are not suitable solely for these groups, however, and may be used more generally in a population.

Treatment can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Administration of more than one dose (typically two doses) is particularly useful in immunologically naïve patients. Multiple doses will typically be administered at least 1 week apart (e.g. about 2 weeks, about 3 weeks, about 4 weeks, about 6 weeks, about 8 weeks, about 12 weeks, about 16 weeks, etc.).

Vaccines of the invention may be administered to patients at substantially the same time as (e.g. during the same medical consultation or visit to a healthcare professional) other vaccines.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

MODES FOR CARRYING OUT THE INVENTION

Individual lots of MF59 adjuvant (50 liters each) were prepared by combining squalene, Span 85, Tween 80, water and citrate buffer. The components were combined in amounts that provide the desired final concentration of 5% (vol) squalene, 0.5% (vol) polysorbate 80, 00.5% (vol) Span 85 and 10 mM citrate buffer. The mixture was microfluidised at about 700 bar, and the final microfluidised mixture was filtered through a 0.2 μm filter.

Figure 1:
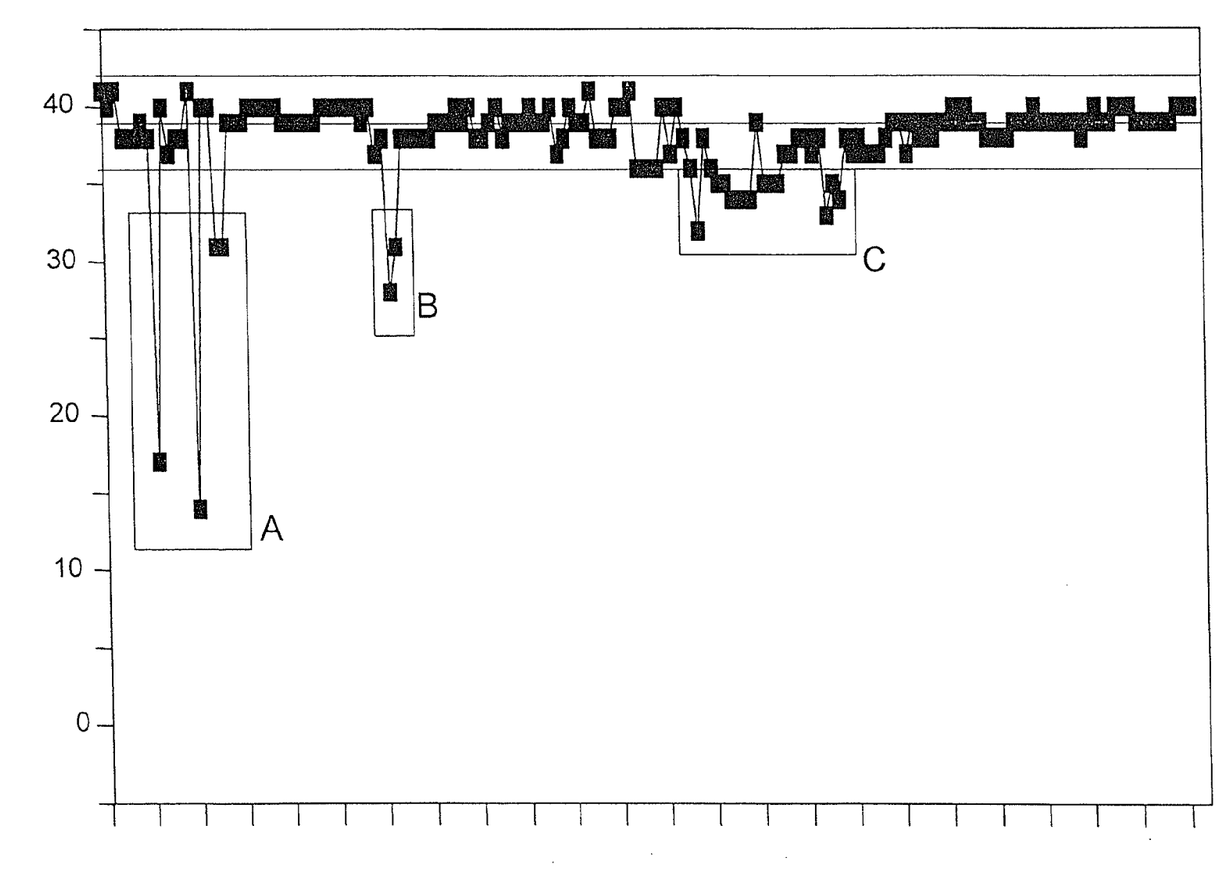
FIG. 1 shows squalene content (mg/ml) for a variety of batches of an oil-in-water emulsion. Three deviations from acceptable squalene content are indicated as A, B and C.

The target squalene content in these MF59 lots was 39±3 mg/ml. FIG. 1 shows the squalene content of over 150 different manufacturing lots. Three deviations from the target range are apparent, labeled A to C. When the manufacturing apparatus was investigated for the 'A' and 'B' lots, it was found that the filter was clogged due to a failed interaction chamber, and the droplet size was also seen to rise outside the target upper level for these lots. Filter clogging was also seen for the 'C' lots, but this time the cause was that an inappropriate filter type had been used, rather than there being a fault with the interaction chamber.

Thus the aberrant squalene levels are suitable for detecting diverse filtration difficulties, without having to inspect the filter directly.

It will be understood that the invention has been described by way of example only and modifications may be made whilst remaining within the scope and spirit of the invention.

REFERENCES (THE CONTENTS OF WHICH ARE HEREBY INCORPORATED BY REFERENCE)

[1] WO90/14837.
[2] Podda & Del Giudice (2003) *Expert Rev Vaccines* 2:197-203.
[3] Podda (2001) *Vaccine* 19: 2673-2680.
[4] *Vaccine Design: The Subunit and Adjuvant Approach* (eds. Powell & Newman) Plenum Press 1995 (ISBN 0-306-44867-X).
[5] *Vaccine Adjuvants: Preparation Methods and Research Protocols* (Volume 42 of *Methods in Molecular Medicine* series). ISBN: 1-59259-083-7. Ed. O'Hagan.
[6] Rothblat et al. (1962) *Anal Biochem* 4:52-6.
[7] Lau et al. (2005)*Lipids* 40(5):523-8.
[8] Spanggord et al. (2002) *J Pharm Biomed Anal* 29(1-2): 183-93.
[9] Choo et al. (2005)*Lipids* 40(4):429-32.
[10] Zambonin et al. (2006) *Rapid Commun Mass Spectrom* 20(2):325-7.
[11] Ko et al. (2002) *J Agric Food Chem* 50(19):5343-8.
[12] Giacometti (2001) *Analyst* 126(4):472-5.
[13] Sulpice & Ferezou (1984) *Lipids* 19(8):631-5.
[14] WO99/056776.
[15] US-2007/0014805.
[16] WO2007/080308.
[17] Suli et al. (2004) *Vaccine* 22(25-26):3464-9.
[18] Huckriede et al. (2003) *Methods Enzymol* 373:74-91.
[19] Hoffmann et al. (2002) *Vaccine* 20:3165-3170.
[20] Subbarao et al. (2003) *Virology* 305:192-200.
[21] Liu et al. (2003) *Virology* 314:580-590.
[22] Ozaki et al. (2004) *J. Virol.* 78:1851-1857.
[23] Webby et al. (2004) *Lancet* 363:1099-1103.
[24] WO97/37000.
[25] Brands et al. (1999) *Dev Biol Stand* 98:93-100.
[26] Halperin et al. (2002) *Vaccine* 20:1240-7.
[27] Tree et al. (2001) *Vaccine* 19:3444-50.
[28] Kistner et al. (1998) *Vaccine* 16:960-8.
[29] Kistner et al. (1999) *Dev Biol Stand* 98:101-110.
[30] Bruhl et al. (2000) *Vaccine* 19:1149-58.
[31] Pau et al. (2001) *Vaccine* 19:2716-21.
[32] http://www.atcc.org/
[33] http://locus.umdnj.edu/
[34] WO03/076601.
[35] WO2005/042728.
[36] WO03/043415.
[37] Williamson et al. (2006) *Infection and Immunity* 74: 961-7.
[38] Loukas et al. (2005) *PLoS Med* 2(10): e295.
[39] EP-A-0139417.
[40] Harper et al. (2004) *Lancet* 364(9447):1757-65.
[41] *J Toxicol Clin Toxicol* (2001) 39:85-100.
[42] Demicheli et al. (1998) *Vaccine* 16:880-884.
[43] Stepanov et al. (1996) *J Biotechnol* 44:155-160.
[44] Berkower et al. (2004) *Virology* 321(1):75-86.
[45] von Brunn et al. (1991) *Vaccine* 9(7):477-84.
[46] Vreden et al. (1991) *Am J Trop Med Hyg* 45(5):533-8.
[47] Moelans et al. (1995) *Mol Biochem Parasitol* 72(1-2): 179-92.

[48] Stoute et al. (1997) *N Engl J Med* 336(2):86-91.
[49] Wunderlich & del Portillo (2000) *Mol Med* 6(3):238-45.
[50] WO01/22992.
[51] Hehme et al. (2004) *Virus Res.* 103(1-2):163-71.
[52] Treanor et al. (1996) *J Infect Dis* 173:1467-70.
[53] Keitel et al. (1996) *Clin Diagn Lab Immunol* 3:507-10.
[54] WO2005/089837.
[55] U.S. Pat. No. 6,692,468.
[56] WO00/07647.
[57] WO99/17820.
[58] U.S. Pat. No. 5,971,953.
[59] U.S. Pat. No. 4,060,082.
[60] EP-A-0520618.
[61] WO98/01174.
[62] Gennaro (2000) *Remington: The Science and Practice of Pharmacy.* 20th edition, ISBN: 0683306472.
[63] Banzhoff (2000) *Immunology Letters* 71:91-96.
[64] WO02/097072.
[65] Nony et al. (2001) *Vaccine* 27:3645-51.
[66] Greenbaum et al. (2004) *Vaccine* 22:2566-77.
[67] Zurbriggen et al. (2003) *Expert Rev Vaccines* 2:295-304.
[68] Piascik (2003) *J Am Pharm Assoc* (Wash. D.C.). 43:728-30.
[69] Mann et al. (2004) *Vaccine* 22:2425-9.
[70] Halperin et al. (1979) *Am J Public Health* 69:1247-50.
[71] Herbert et al. (1979) *J Infect Dis* 140:234-8.
[72] Chen et al. (2003) *Vaccine* 21:2830-6.

The invention claimed is:

1. A method for controlling the quality of an oil-in-water emulsion adjuvant, which comprises squalene and an aqueous carrier as components, by determining whether said oil-in-water adjuvant has an acceptable level of squalene, said method comprises:
    preparing the oil-in-water emulsion by placing the components of the oil-in-water emulsion in a microfluidizer and microfluidizing the components to form a microfluidized mixture;
    (ii) filtering the microfluidized mixture through a filter to provide the oil-in-water emulsion and forming the oil-in-water adjuvant;
    (iii) measuring the actual squalene content in said oil-in-water emulsion adjuvant;
    (iv) comparing the actual squalene content in said oil-in-water emulsion adjuvant with a standard squalene content;
    (v) rejecting said oil-in-water emulsion adjuvant if the actual squalene content of said oil-in-water emulsion adjuvant differs from the standard squalene content by more than plus or minus 10%.

2. The method according to claim 1, wherein the components of the oil-in-water emulsion further comprise a surfactant.

3. The method according to claim 1 wherein the oil-in-water emulsion in the oil-in-water adjuvant is a submicron emulsion.

4. The method according to claim 3, wherein the components of oil-in-water emulsion adjuvant further comprise polyoxyethylenesorbitan monooleate and sorbitan trioleate.

5. The method according to claim 1, wherein the components of the oil-in water emulsion further comprises a tocopherol and polyoxyethylenesorbitan monooleate.

6. The method of claim 1, wherein the components of the emulsion in the oil-in water emulsion further comprises a tocopherol and t-octylphenoxypolyethoxyethanol.

7. The method of claim 1, wherein the components of the oil-in water emulsion further comprises a polyoxyethylene alkyl ether hydrophilic nonionic surfactant and a hydrophobic nonionic surfactant.

8. The method of claim 1, wherein if the oil-in-water emulsion adjuvant has an acceptable level of squalene content, the method further comprises the further step of (v) combining the oil-in-water adjuvant with an antigen.

9. The method of claim 8, wherein the antigen is an influenza antigen.

10. The method of claim 1, wherein the standard squalene content is a squalene concentration between 2% and 8% by volume.

11. The method of claim 10, wherein the standard squalene content is a squalene concentration between 4% and 6% by volume.

* * * * *